United States Patent [19]

Babin et al.

[11] Patent Number: 5,434,175

[45] Date of Patent: Jul. 18, 1995

[54] PYRETHRINOID ESTERS DERIVED FROM ISOXAZOLIC OR ISOTHIAZOLIC ALCOHOL, THEIR PREPARATION PROCESS AND THEIR USE AS PESTICIDES

[75] Inventors: Didier Babin, Montigny; Marc Benoit, Roquevaire; Jean P. Demoute, Neuilly Plaisance, all of France

[73] Assignee: Roussel Uclaf, France

[21] Appl. No.: 133,015

[22] PCT Filed: Feb. 5, 1993

[86] PCT No.: PCT/FR93/00119

§ 371 Date: Oct. 7, 1993

§ 102(e) Date: Oct. 28, 1993

[87] PCT Pub. No.: WO93/16054

PCT Pub. Date: Oct. 19, 1993

[30] Foreign Application Priority Data

Feb. 7, 1992 [FR] France .................. 92 01392

[51] Int. Cl.⁶ .................. C07D 261/08; A01N 43/80
[52] U.S. Cl. .................. 514/378; 514/372; 548/214; 548/247
[58] Field of Search ............... 548/214, 247; 514/372, 514/378

[56] References Cited

U.S. PATENT DOCUMENTS 4,833,163  5/1989  Martel .................. 514/531

OTHER PUBLICATIONS

Lel, Pestic Sci 7, 288, (1976).

Primary Examiner—Robert Gerstl
Attorney, Agent, or Firm—Bierman and Muserlian

[57] ABSTRACT

A pyrethinoid pesticide of the formula:

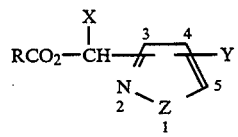

where Z is O or S and R is the residue of a pyrethinoic acid has been prepared.

19 Claims, No Drawings

PYRETHRINOID ESTERS DERIVED FROM ISOXAZOLIC OR ISOTHIAZOLIC ALCOHOL, THEIR PREPARATION PROCESS AND THEIR USE AS PESTICIDES

This application is a 371 of PCT/FR93/00119 filed Feb. 5, 1993.

The present invention relates to new pyrethrinoid esters derived from isoxazolic or isothiazolic alcohol, their preparation process and their use as pesticides.

A subject of the invention is, in all their possible stereoisomer forms as well as their mixtures, the compounds of formula (I):

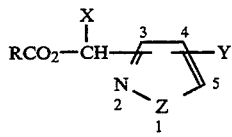

in which
the

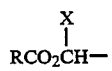

radical is in position 3 or 5,

X represents a hydrogen atom, a cyano radical or a linear or branched, saturated or unsaturated alkyl radical containing up to 4 carbon atoms, Y in position 4 or 5 represents a hydrogen atom, an $NO_2$, $NH_2$, $C\equiv N$ radical, a saturated or unsaturated, linear or branched alkyl radical containing up to 8 carbon atoms optionally substituted by one or more halogen atoms, a $(CH_2)_nOH$ radical the OH radical of which can be optionally etherified or esterified, n representing the number 0, 1, 2, 3 or 4 or a

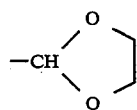

radical, or an $NHalk_1$ or

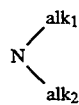

radical in which $alk_1$ and $alk_2$, identical or different, represent an alkyl radical containing up to 8 carbon atoms, Z represents an oxygen or sulphur atom, and either R represents a radical:

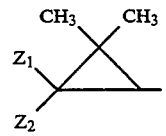

in which:

$Z_1$ and $Z_2$ each represent a methyl radical, or $Z_1$ represents a hydrogen atom and either $Z_2$ represents a radical:

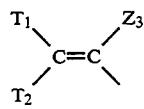

in which $Z_3$ represents a hydrogen or halogen atom and $T_1$ and $T_2$, identical or different, represent a hydrogen atom, a halogen atom, a saturated or unsaturated alkyloxy or alkyl radical containing 1 to 8 carbon atoms optionally substituted by halogens, a mono-, di- or trifluoromethyl or cyano radical or a phenyl nucleus optionally substituted by a halogen, or $T_1$ and $T_2$ form together a cycloalkyl radical containing 3 to 6 carbon atoms or a radical:

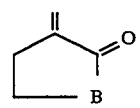

in which B represents an oxygen or sulphur atom; or $Z_2$ represents a radical:

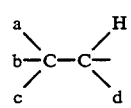

in which a, b, c and d, identical or different, each represent a halogen atom,
or $Z_2$ represents a radical:

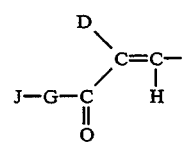

in which D represents a hydrogen or halogen atom, an alkyloxy radical containing 1 to 8 carbon atoms, G represents an oxygen or sulphur atom and J represents either a saturated or unsaturated, linear, branched or cyclic alkyl radical containing 1 to 8 carbon atoms, optionally substituted by one or more identical or different functional groups, or an aryl group containing 6 to 14 carbon atoms, optionally substituted by one or more identical or different functional groups, or a heterocyclic radical optionally substituted by one or more identical or difference functional groups, or R represents a radical:

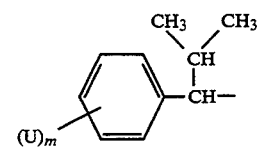

in which U, in any position on the benzene nucleus, represents a halogen atom, an alkyl radical containing 1 to 8 carbon atoms or an alkoxy radical containing 1 to 8 carbon atoms, m representing the number 0, 1 or 2 and when m is 2, the U substituents can be identical or different.

When X represents an alkyl radical, it is preferably a methyl, ethyl or ethynyl radical.

When Y represents an alkyl radical, it is preferably one of the following radicals: methyl, ethyl, isopropyl, n-butyl, isobutyl, terbutyl, vinyl, allyl, ethynyl or propynyl.

When Y is substituted by a halogen atom, the halogen is preferably fluorine or chlorine, it can be for example the CF$_3$, CHF$_2$, CHCl$_2$, CH$_2$F radical or also the

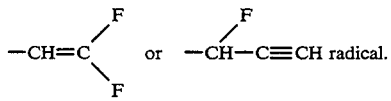

When Y represents an O-alkyl radical, the alkyl preferably has one of the values indicated above.

When Y represents a free, etherified or esterified —(CH$_2$)$_n$OH radical, it is preferably the —CH$_2$OH, —CH$_2$OCH$_3$ or —CH$_2$OCOCH$_3$ radical.

When T$_1$, T$_2$ or Z$_3$ represents a halogen atom, it is preferably a fluorine, chlorine or bromine atom.

When T$_1$ or T$_2$ represents an alkyl or alkyloxy radical, it is preferably a methyl, ethyl, propyl, methoxy, ethoxy or propoxy radical.

a, b, c and d preferably represent a chlorine or bromine atom.

When D represents a halogen atom, it is preferably a fluorine, chlorine or bromine atom.

When J represents an alkyl radical substituted by one or more functional groups, by alkyl is preferably meant a radical containing 1 to 8 carbon atoms such as, for example, the methyl, ethyl, propyl, isopropyl, butyl, isobutyl or tert-butyl radical and by functional group is meant one of those mentioned in the European Application published under the number 50534.

J can also represent an alkyl radical substituted by an aryl radical, in particular an optionally substituted phenyl radical.

When J represents an alkyl radical substituted by one or more functional groups, the following radicals can be mentioned as preferred values of J:

—(CH$_2$)$_{n1}$—C(Hal)$_3$ in which n1 is an integer from 1 to 8 and Hal is a halogen atom, for example the —CH$_2$—CCl$_3$, —CH$_2$—CF$_3$, —CH$_2$—CH$_2$—CCl$_3$ or CH$_2$—CH$_2$—CF$_3$ radical;

—(CH$_2$)$_{n2}$—CH(Hal)$_2$ in which Hal is defined as above and n2 is a number from 0 to 8, for example the —CH$_2$CHCl$_2$, —CH$_2$—CHF$_2$ or —CHF$_2$ radical;

—(CH$_2$)$_{n1}$—CH$_2$(Hal) in which n1 and Hal are defined as above, for example the —CH$_2$—CH$_2$Cl or —CH$_2$—CH$_2$F radical, —C(CHal$_3$)$_3$ in which Hal is defined as above, for example one of the following radicals: —C(CF$_3$)$_3$, —C(CF$_3$)$_2$—CCl$_3$, —C(CF$_3$)$_2$—CH$_3$, —C(CH$_3$)$_2$—CF$_3$ or —C(CH$_3$)(CF$_3$)—CH$_2$—CH$_3$, —CH(CF$_3$)—CH$_3$ or —CH(CF$_3$)$_2$, —C(CH$_3$)$_2$—CN, —CH(CH$_3$)—CN or —(CH$_2$)$_n$—CN in which n is defined as previously, —CH(CN)—C(Hal)$_3$ in which Hal is defined as previously, for example the radical: —CH(CN)-CCl$_3$ —(CH$_2$)$_{n1}$—OR$_a$, in which n1 is defined as previously and R$_a$ represents a hydrogen atom or a linear or branched alkyl radical containing 1 to 8 carbon atoms, for example the —CH$_2$—OCH$_3$, —CH$_2$—CH$_2$—O—CH$_3$, —CH$_2$—CH$_2$—O—CH$_2$—CH$_3$ or —CH$_2$—CH$_2$—OH radical;

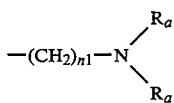

in which n1 and R$_a$ are defined as previously and the two R$_a$ radicals can be different from each other, for example the radical:
—CH$_2$—CH$_2$—NH—CH$_3$, —CH$_2$—CH$_2$—N(CH$_3$)$_2$ or —CH$_2$—CH$_2$—N(CH$_3$)—CH$_2$—CH$_3$;

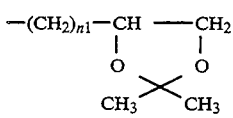

in which n1 is defined as previously, for example the radical:

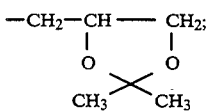

—(CH$_2$)$_{n1}$—CH(OH)—CH$_2$—OH
in which n1 is defined as previously, for example the radical:
—CH$_2$—CH(OH)—CH$_2$—OH;   —(CH$_2$)$_{n1}$—O—THP
in which n1 is defined as previously and THP represents the 2-tetrahydropyrannyl radical, for example the radical: —CH$_2$—O—THP or —CH$_2$—CH$_2$—O—THP;

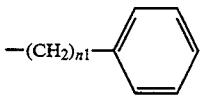

in which n1 is defined as previously, for example the benzyl or phenethyl radical;

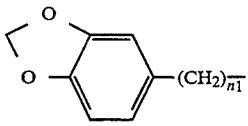

in which n1 is defined as previously, for example the radical:

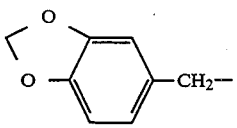

When J represents an optionally substituted aryl radical, it is preferably an optionally substituted phenyl radical.

When J represents a heterocyclic radical, it is preferably the pyridyl, furyl, thienyl, oxazolyl or thiazolyl radical.

A more particular subject of the invention is the compounds of formula (I) in which Z represents an oxygen atom.

Among the preferred compounds of the invention, there can be mentioned:

the compounds of formula (I) in which the $$\overset{X}{\underset{|}{RCO_2CH}}$$

radical is in position 3;

the compounds of formula (I) in which X represents an ethynyl radical;

the compounds of formula (I) in which X represents a hydrogen atom;

the compounds of formula (I) in which Y is in position 5;

the compounds of formula (I) in which Y represents an alkyl radical containing up to 4 carbon atoms optionally substituted by one or more halogen atoms, for example a $CHF_2$, $CF_3$, $CH_3$, $CH_2F$ or —CHF—C≡CH radical;

the compounds of formula (I) in which R represents the radical:

$$\underset{Cl}{\overset{F_3C}{\diagdown}}C=CH-\!\!\!\bigtriangleup\!\!\overset{H_3C\quad CH_3}{}$$

in all their possible stereoisomer forms as well as their mixtures;

the compounds of formula (I) in which R represents a radical:

$$\underset{CO_2alk_1}{\diagup}=C-\!\!\!\bigtriangleup\!\!\overset{H_3C\quad CH_3}{}$$

in which $alk_1$ represents an alkyl radical containing up to 4 carbon atoms optionally substituted by one or more fluorine atoms;

the compounds of formula (I) in which R represents $$\underset{CO_2alk_2}{\overset{F}{\diagdown}}=C-\!\!\!\bigtriangleup\!\!\overset{H_3C\quad CH_3}{}$$

in which $alk_2$ represents an alkyl radical containing up to 4 carbon atoms optionally substituted by one or more fluorine atoms.

Among the preferred compounds of the invention, there can be mentioned in particular the compounds whose preparation is given hereafter in the experimental part and quite particularly the products of Examples 2, 6, 7, 32, 33 and 34.

Also a subject of the invention is a preparation process for the compounds of formula (I) characterized in that an acid of formula (II):

$$RCO_2H \qquad (II)$$

in which R is defined as previously, or a functional derivative of this acid is subjected to the action of an alcohol of formula (III):

$$\overset{X}{\underset{|}{HO-CH}}\!\!-\!\!\!\underset{N_{\diagdown Z}}{\diagup\!\!\!-\!\!\!Y}\qquad (III)$$

in which X, Y and Z are defined as previously, in order to obtain the corresponding compound of formula (I).

The acid functional derivative used is preferably an acid chloride.

When the acid of formula (II) is reacted with the alcohol of formula (III), the operation is preferably carried out in the presence of dicyclohexylcarbodiimide.

The acids of formula (II) used are known products used in the synthesis of pyrethrinoid compounds.

(5-methyl 3-isoxazol) methanol is a commercially-sold product, some of the alcohols of formula (III), in particular those whose preparation is given hereafter in the experimental part, are new products and are themselves a subject of the present invention.

The alcohols of formula (III) can be prepared according to the following process:

$$H_2NCH_2CO_2alk \xrightarrow[2)\ H-C\equiv CH_2-Hal]{1)\ NaNO_2/HCl} \underset{N_{\diagdown O}}{\diagup\!\!\!-\!\!\!\overset{CO_2alk}{}}\!\!-\!\!Hal$$

$$\downarrow$$

alk: 1–4C alkyl
Hal: halogen $$\underset{N_{\diagdown O}}{\diagup\!\!\!-\!\!\!\overset{CO_2alk}{}}\!\!-\!\!CHO$$

$$\downarrow$$

$$alcohol \leftarrow \underset{N_{\diagdown O}}{\diagup\!\!\!-\!\!\!\overset{CHO}{}}\!\!-\!\!CHF_2 \leftarrow \underset{N_{\diagdown O}}{\diagup\!\!\!-\!\!\!\overset{CO_2alk}{}}\!\!-\!\!CHF_2$$

or also according to the following process:

$$\underset{N_{\diagdown O}}{\diagup\!\!\!-\!\!\!\overset{HOH_2C}{}}\!\!-\!\!CH_2Br$$

$$\downarrow\ \overset{DAST}{CH_2Cl_2}$$

-continued

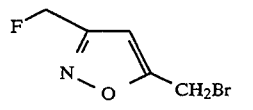

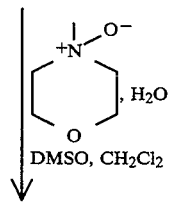

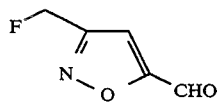

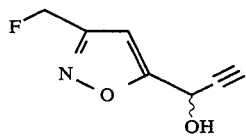

The compounds of formula (III) in which Z represents a sulphur atom can be prepared according to the following processes:

A)

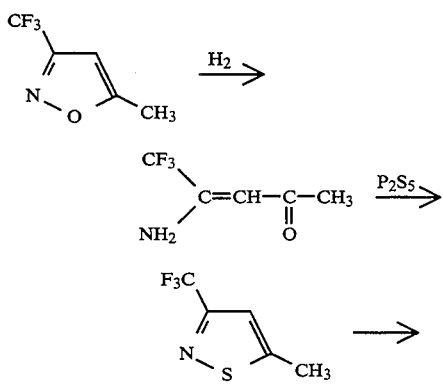

-continued

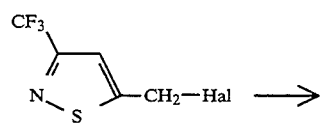

conversion into the alcohol according to the diagram given above when Z represents an oxygen atom.

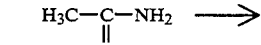

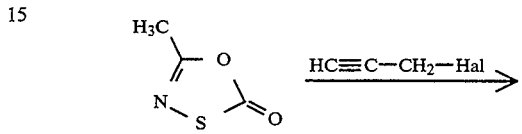

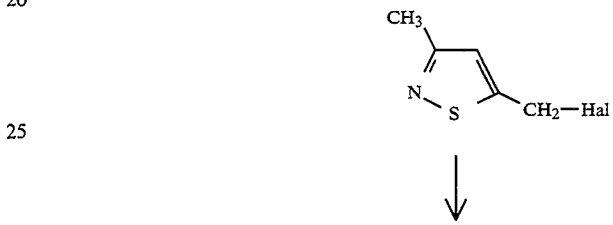

alcohol

The compounds of formula (III) in which the Y radical is in position 3 can be prepared according to the following process:

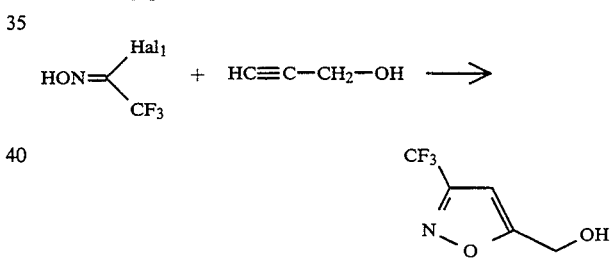

The compounds of formula (III), in which the Y radical is in position 5, can be prepared according to the following process:

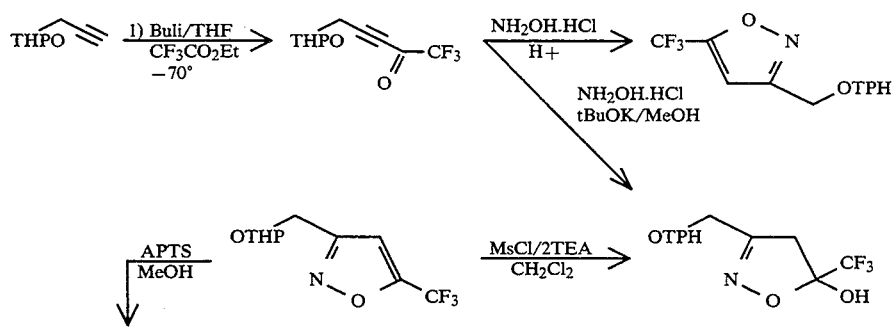

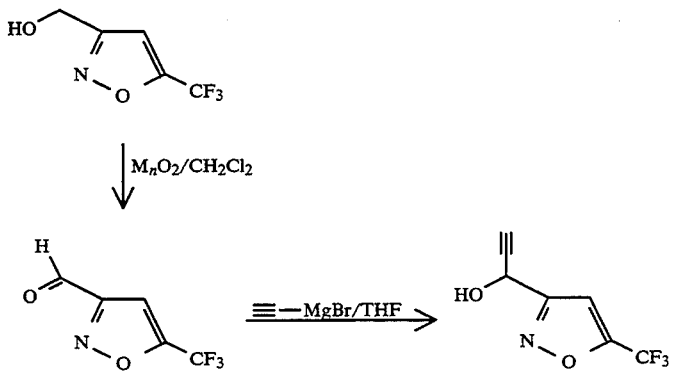

Also a subject of the invention is a variant of the preceding process characterized in that a compound of formula (IV):

in which alk represents an alkyl radical containing up to 4 carbon atoms and $Hal_1$ represents a halogen atom, is subjected to the action of a compound of formula (V):

in which $Hal_2$ represents a halogen atom, in order to obtain the compound of formula (VI):

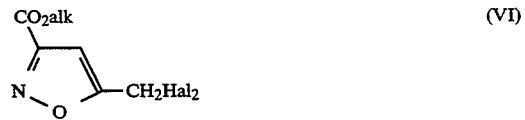

then the compound of formula (VI) thus obtained is subjected to the following different stages in any order:
- conversion in one or two stages of the ester function into an aldehyde function, then into an alcohol function optionally with the introduction of an X radical which is different from hydrogen,
- conversion of the $CH_2OH$ radical into the desired Y radical,
- condensation of the heterocyclic alcohol obtained and of the acid of formula (II), in order to obtain the corresponding compound of formula (I).

The condensation reaction of the products of formula (IV) and formula (V) preferably takes place in a basic medium.

The conversion of the ester function into an aldehyde takes place according to standard processes, for example in the presence of diisobutylaluminium hydride (DIBAH) or an equivalent reagent.

The conversion of the intermediate aldehyde into the $HC \equiv C-CH_2-OH$ radical is carried out using ethynyl magnesium bromide.

The introduction of the Y radical can be carried out firstly by converting the $CH_2Hal$ radical into the CHO radical, using an oxidizing agent such as for example 4-methyl morpholine N-oxide, then by reacting the appropriate reagent on this aldehyde, for example diethylaminosulphide trifluoride (DAST), when it is desired to obtain a compound in which Y represents a $CHF_2$ radical.

The products of formula (VI) are new products and are in themselves a subject of the present invention.

A more particular subject of the invention is the compound of formula (VI) whose preparation is given in the experimental part.

The compounds of formula (I) have useful properties which allow their use for combating parasites. It may be for example for combating parasites of vegetation, parasites in premises and parasites of warm-blooded animals.

Thus it is that the products of the invention can be used to combat parasitic insects, nematodes and acaridae of vegetation and animals.

A particular subject of the invention is the use of the compounds of formula (I) for combating parasites of vegetation, parasites in premises and parasites of warm-blooded animals.

The products of formula (I) can also be used for combating insects and other parasites of the soil, for example Coleoptera, such as Diabrotica, click beetles and May beetle grubs, Myriapoda such as scutigeridae and blanjules, and Diptera such as cecydomia and Lepidoptera such as owlet moths.

They are used at doses comprised between 10 g and 300 g of active ingredient per hectare.

The products of formula (I) can also be used to combat insects in premises, to combat in particular flies, mosquitoes and cockroaches.

The products of formula (I) are more photostable and are not very toxic to mammals.

All of these properties mean that the products of formula (I) correspond perfectly to the requirements of the modern agrochemical industry: they allow crops to be protected while preserving the environment.

The products of formula (I) can also be used to combat parasitic acaridae and nematodes of vegetation.

The compounds of formula (I) can also be used to combat parasitic acaridae of animals, to combat for example ticks and notably ticks of Boophilus type, those of Hyalomnia type, those of Amblyomnia type and those of Rhipicephalus type or to combat all sorts of mites and notably the sarcoptic mite, the psoroptic mite and the chorioptic mite.

Therefore a subject of the invention is also the compositions intended for combating parasites of warm-blooded animals, parasites in premises and of vegetation, characterized in that they contain at least one of the products of formula (I) defined above and notably the products of formula (I) of Examples 2, 6, 7, 32, 33 and 34.

A particular subject of the invention is the insecticide compositions containing as active ingredient at least one of the products defined above.

These compositions are prepared according to the usual processes of the agrochemical industry or the veterinary industry or the industry for products intended for animal fodder.

In these compositions intended for agricultural use and for use in premises, the active ingredient or ingredients can optionally have added to them one or more other pesticide agents. These compositions can appear in the form of powders, granules, suspensions, emulsions, solutions, aerosol solutions, combustible strips, baits or other preparations usually for the use of this type of compound.

In addition to the active ingredient, these compositions contain, in general, a vehicle and/or a surface active agent, non-ionic, ensuring, moreover, a uniform dispersion of the constitutive substances of the mixture. The vehicle used can be a liquid, such as water, alcohol, hydrocarbons or other organic solvents, a mineral, animal or vegetable oil, a powder such as talc, clays, silicates, kieselguhr or a combustible solid.

The insecticide compositions according to the invention preferably contain from 0.005% to 10% by weight of active ingredient.

According to an advantageous operating method, for use in premises, the compositions according to the invention are used in the form of fumigant compositions.

The compositions according to the invention can then be advantageously constituted, for the non-active part, by a combustible insecticide coil, or also by an incombustible fibrous substrate. In the latter case, the fumigant obtained after incorporation of the active ingredient is placed on a heating apparatus such as an electric vaporizer.

In the case where an insecticide coil is used, the inert support can be, for example, pyrethrum marc compound, Tabu powder (or Machilus Thumbergii leaf powder), pyrethrum stem powder, cedar leaf powder, sawdust (such as pine sawdust) starch and coconut shell powder.

The dose of active ingredient can then be, for example, from 0.03 to 1% by weight.

In the case where an incombustible fibrous support is used, the dose of active ingredient can then be, for example, from 0.03 to 95% by weight.

The compositions according to the invention for use in premises can also be obtained by preparing a sprayable oil based on the active ingredient, this oil soaking the wick of a lamp and then being set alight.

The concentration of active ingredient incorporated in the oil is, preferably, 0.03 to 95% by weight.

Also a subject of the invention is the acaricide and nematicide compositions containing as active ingredient at least one of the products of formula (I) defined above.

The insecticide compositions according to the invention, as acaricide and nematicide compositions, can optionally have added to them one or more other pesticide agents. The acaricide and nematicide compositions can appear notably in the form of powder, granules, suspensions, emulsions, solutions.

For acaricide use, wettable powders are preferably used, for foliar spraying, containing 1 to 80% by weight of active ingredient or liquids for foliar spraying containing 1 to 500 g/l of active ingredient. Powders can also be used for foliar dusting containing 0.05 to 3% of active ingredient.

For nematicide use, liquids are preferably used for soil treatment containing 300 to 500 g/l of active ingredient.

The acaricide and nematicide compounds according to the invention are used, preferably, at doses comprised between 1 and 100 g of active ingredient per hectare.

In order to enhance the biological activity of the products of the invention, they can be added to standard synergists used in such a case such as 1-(2,5,8-trioxadodecyl) 2-propyl 4,5-methylenedioxy benzene (or piperonyl butoxide) or N-(2-ethyl heptyl) bicyclo [2,2-1] 5-heptene-2,3-dicarboximide, or piperonyl-bis-2-(2'-n-butoxy ethoxy) ethylacetal (or tropital).

The compounds of formula (I) have an excellent general tolerance, and therefore a subject of the invention is also the products of formula (I), for combating in particular affections caused by ticks and mites in man and in animals.

The products of the invention are notably used to combat lice as a preventative or curative and to combat scabies.

The products of the invention can be administered by external route, by spraying, by shampooing, by bathing or painting on.

The products of the invention for veterinary use can also be administered by painting the dorsal spine according to the so-called "pour-on" method.

It can also be indicated that the products of the invention can be used as biocides or as growth regulators.

A subject of the invention is also the combinations endowed with insecticide, acaricide or nematicide activity, characterized in that they contain as active ingredient, on the one hand at least one of the compounds of general formula (I), and on the other hand at least one of the pyrethrinoid esters chosen from the group constituted by the esters of allethrolone, of 3,4,5,6-tetrahydrophthalimidomethyl alcohol, of 5-benzyl-3-furyl methyl alcohol, of 3-phenoxybenzyl alcohol and of alpha-cyano-3-phenoxybenzyl alcohol with chrysanthemic acids, by the esters of 5-benzyl-3-furyl methyl alcohol with 2,2-dimethyl-3-(2-oxo-3-tetrahydrothiophenylidenemethyl)-cyclopropanecarboxylic acids, by the esters of 3-phenoxybenzyl alcohol and of alpha-cyano-3-phenoxybenzyl alcohol with 2,2-dimethyl-3-(2,2-dichloro-vinyl)-cyclopropanecarboxylic acids, by the esters of alphacyano-3-phenoxy-benzyl alcohol with 2,2-dimethyl-3-(2,2-dibromovinyl)-cyclopropanecarboxylic acids, by the esters of 3-phenoxybenzyl alcohol with 2-parachlorophenyl-2-isopropyl acetic acids, by the esters of allethrolone, of 3,4,5,6-tetrahydrophthalimidomethyl alcohol, of 5-benzyl-3-furyl methyl alcohol, of 3-phenoxybenzyl alcohol, and of alphacyano-3-phenoxybenzyl alcohol with 2,2-dimethyl-3-(1,2,2,2-tetrahaloethyl)-cyclopropanecarboxylic acids, in which "halo" represents a fluorine, chlorine or bromine atom, it being understood that the compounds (I) can exist in all their possible stereoisomer forms as well as the acid and alcohol copulas of the above pyrethrinoid esters.

The following examples illustrate the invention without however limiting it.

EXAMPLE 1

(5-methyl-3-isoxazolyl) methyl [1R-[1alpha,3alpha(Z)]]-3-(2-chloro-3,3,3-trifluoro-1-propenyl)-2,2-dimethylcyclopropanecarboxylate.

A solution containing 1.10 g of dicyclohexylcarbodiimide (DCC) and 5 cm$^3$ of methylene chloride is added at 0° C. to a solution containing 0.6 g of 5-methyl-3-isoxazol methanol, 13 cm³ of methylene chloride, 1.3 g of 1R[1alpha,3alpha(Z)] 2,2-dimethyl 3-(3,3,3-trifluoro 2-chloropropenyl) cyclopropane carboxylic acid and 0.032 g of dimethylaminopyridine (DMAP). The temperature of the reaction medium is allowed to return to 20° C., and the medium is maintained under agitation at 20° C. for 17 hours. The medium is filtered, rinsed with methylene chloride and brought to dryness under reduced pressure. 2.03 g of product is obtained which is chromatographed on silica, eluting with a hexane-isopropyl ether mixture (7-3). In this way 1.62 g of the desired product is obtained.

| NMR CDCl₃ | |
| --- | --- |
| H of the twinned methyls | 1.30 and 1.31 |
| H in position 1 of the cyclopropane | 2.04−(d, J=8.5Hz) |
| H in position 3 of the cyclopropane | 2.20(m) |
| H of the CH₃ of the isoxazole | 2.43(d) |
| H of the CH₂ in alpha position of the CO₂ | 5.13(s) |
| aromatic H | 6.00(q)(J=1Hz) |
| ethylenic H | 6.90 |

EXAMPLES 2 TO 5

By operating as in Example 1 starting with corresponding acids and alcohols, the following products were obtained:

EXAMPLES 2

(5-methyl-3-isoxazolyl) methyl [1R-[1alpha,3alpha(Z)]]-3-(3-ethoxy-2-fluoro-3-oxo-1-propenyl)-2,2-dimethylcyclopropanecarboxylate.

| NMR | |
| --- | --- |
| H of the twinned methyls | 1.28(s) |
| H of CO₂Et | 1.35(t)—4.31(q) |
| H in position 1 of the cyclopropane | 1.95(d, J=8.5 Hz) |
| H in position 3 of the cyclopropane | 2.90(m) |
| H of the CH₃ of the isoxazole | 2.43(s) |
| H of the CH₂ in alpha position of the carboxyl | 5.12(s) |
| aromatic H | 6.01(s) |
| ethylenic H | 6.40(dd, J=10 and 21Hz). |

EXAMPLE 3

(3-trifluoromethyl-5-isoxazolyl) methyl [1R-1alpha,3alpha (Z)]]-3-(2-chloro-3,3,3-trifluoro-1-propenyl)-2,2-dimethylcyclopropanecarboxylate.

| NMR | |
| --- | --- |
| twinned CH₃'s | 1.30(s) and 1.32(s) |
| H₁ | 2.04(d, J:8.5Hz) |
| H₃ | 2.25(m) |
| H of CO₂CH₂ | 5.24 [A,B] |
| H of the isoxazole | 6.57(s) |
| ethylenic H (Z) | 6.85(d, J=9.5Hz) |

EXAMPLE 4

(3-trifluoromethyl-5-isoxazolyl) methyl [1R-[1alpha,-3alpha(Z)]]-3-(3-ethoxy-2-fluoro-3-oxo-1-propenyl)-2,2-dimethylcyclopropanecarboxylate.

| NMR | |
| --- | --- |
| H of the twinned methyls | 1.27(s) and 1.30(s) |
| H of CO₂ CH₂ CH₃ | 1.36(t) |
| H of CO₂ CH₂ CH₃ | 4.31(q) |
| ethylenic H E | 6.34(dd, J=10 and 20.5Hz) |
| isoxazole H | 6.56(s) |
| H₁ | 1.96(d, J=8.5Hz) |
| H₃ | 2.94(m) |

EXAMPLE 5

(3-trifluoromethyl-5-isoxazolyl) methyl [1R-[1alpha,-3alpha(Z)]]-2,2-dimethyl-3-[3-oxo-3-[2,2,2-trifluoro-1-(trifluoromethyl) ethoxy]-1-propenyl] cyclopropanecarboxylate.

| NMR CDCl₃ | |
| --- | --- |
| H of the twinned methyls | 1.33 |
| H₁ and H₃ | 2.11(d, J=8.5Hz) and 3.20(m) |
| H of CO₂CH₂— | 5.24(m) |
| H of CH(CF₃)₂ | 5.81 |
| H of the Delta Z double bond | 6.04(d, J=11.5Hz) and 6.91(m) |
| aromatic H | 6.56(s) |

Preparation 1

3-(trifluoromethyl)-5-isoxazolemethanol.

Stage A: trifluoroacetaldehyde oxime.

62.9 cm³ of a 32% soda solution is introduced over one hour at 20° C. to a solution containing 37.1 g of 2,2,2-trifluoro 1,1-ethanediol, 60 cm³ of methanol, 100 cm³ of a water and ice mixture and 25 g of hydroxylamine hydrochloride. The reaction mixture is maintained under agitation for 16 hours at 20° C. It is brought to pH 6 by the addition of concentrated hydrochloric acid. Extraction is carried out with ethyl ether, the extracts are dried and the residue is chromatographed on silica eluting with a hexane-ethyl acetate mixture (7-3).

The 2 fractions obtained are taken up with 160 cm³ of a 2N soda solution, extracted with ethyl ether, and acidified to pH 6. After drying and distilling, 19.2 g of product is obtained, B p: 78°–84° C. which is used as it is in the following stage.

Stage B: 2,2,2-trifluoro N-hydroxy ethanimidoyl bromide.

A solution containing 19 g of the product obtained in Stage A and 30 cm³ of dimethylformamide is introduced at 20° C. into a solution containing 31.4 g of N-bromosuccinimide and 90 cm³ of dimethylformamide. The reaction mixture is maintained under agitation for 4 hours at 20° C. It is poured into an iced water mixture, extracted with isopropyl ether, and the extracts are washed and dried. In this way 37.55 g of product (B.p.: 64° C./76 mbars) is obtained which is used as it is in the following stage.

Stage C: (3-trifluoromethyl 5-isoxazol) methanol.

A solution containing 22.7 cm³ of triethylamine and 70 cm³ of toluene is introduced at about 20°–25° C. over one hour 30 minutes into a solution containing 30 g of the product prepared in Stage B and 14.2 ml of propargyl alcohol in 80 cm³ of toluene. The reaction mixture is maintained under agitation for 20 hours at 20° C. It is poured into an aqueous solution of potassium acid phosphate, extracted with ethyl ether, the extracts are washed with water, dried and evaporated to dryness. 9.7 g of product is obtained which is chromatographed on silica, eluting with a methylene chloride-ethyl acetate mixture (9-1). 3 g of desired product is obtained, Rf: 0.25.

EXAMPLE 6

1-[5-(difluoromethyl)-3-isoxazolyl] 2-propynyl 1R[1alpha,3alpha(Z)] 2,2-dimethyl-3-(3,3,3- trifluoro-2-chloropropenyl) cyclopropane carboxylate.

Stage A: Ethyl 5-bromomethyl 3-isoxazol carboxylate.

22.24 cm$^3$ of 3-bromo 1-propyne is added at 0° to 15.46 g of ethyl chloro-(hydroxyimino) acetate. The reaction mixture is maintained under agitation at 0° C. for 10 minutes and 15.17 cm$^3$ of triethylamine and 35 cm$^3$ of isopropyl ether are added over 17 hours at 0°/+4° C. The reaction mixture is then maintained under agitation at 0° C. for 20 minutes. The precipitate obtained is separated off, rinsed, and the liquid phase is poured into an aqueous solution of potassium acid phosphate. Extraction is carried out with isopropyl ether, the extracts are washed, dried, filtered, rinsed and brought to dryness under reduced pressure. 24.92 g of a product is obtained which is chromatographed on silica. 19.09 g of desired product is obtained.

Stage B: (bromomethyl) 3-isoxazol 5-carboxaldehyde.

66 cm$^3$ of diisobutyl aluminium hydride (DIBAH) is added at −70° C. over 30 minutes to a solution containing 11.51 g of the product obtained in Stage A and 345 cm$^3$ of toluene. The reaction mixture obtained is agitated at −70° C. for 2 hours. 300 cm$^3$ of a molar solution of sodium and potassium double tartrate is added, allowing the temperature to rise to 20° C. The reaction mixture is agitated for 2 hours, then decanted and extracted with ethyl acetate. The extracts are dried, filtered, rinsed and brought to dryness. 10.09 g of product is obtained which is chromatographed on silica, eluting with a hexane-ethyl acetate mixture (75-25). In this way 7.52 g of desired product is obtained.

Stage C: 5-(bromomethyl) alpha-ethynyl 3-isoxazol methanol.

75 cm$^3$ of ethynyl magnesium bromide is added at 0° C. to a solution containing 9.52 g of the product prepared in Stage B and 100 cm$^3$ of tetrahydrofuran. The reaction mixture is agitated at 20° C. for 2 hours 30 minutes. It is poured into a mixture of water, ice and ammonium chloride. Extraction is carried out with isopropyl ether, and the extracts are saturated with sodium chloride. They are dried, filtered, rinsed and brought to dryness under reduced pressure. 13.01 g of product is obtained which is chromatographed on silica, eluting with a hexane-ethyl acetate mixture (7-3). 8.71 g of desired product is obtained.

Stage D: 3-(1-hydroxy-propynyl) isoxazol-5-carboxaldehyde.

9.8 g of 4-methyl morpholine oxide, 68 cm$^3$ of dimethylsulphoxide and 34 cm$^3$ of methylene chloride are added at 0° C. to a solution containing 4 g of the product prepared in Stage C and 30 cm$^3$ of methylene chloride. The mixture is allowed to return to 20° C. and agitated for 5 hours. It is poured into an aqueous solution of potassium acid phosphate. Extraction is carried out with ethyl acetate, the extracts are dried, filtered and brought to dryness. 8.18 g of product is obtained which is chromatographed on silica, eluting with a hexane-ethyl acetate mixture (1-1). In this way 1.96 g of desired product is obtained.

Stage E: 1-[5-formyl-3-isoxazol] 2-propynyl 1R[1alpha,3alpha(Z)] 2,2-dimethyl 3-(3,3,3-trifluoro-2-chloropropenyl) cyclopropane carboxylate.

A mixture of 1.59 g of 1R[1alpha,3alpha(Z)] 2,2-dimethyl 3-(3,3,3-trifluoro 2-chloropropenyl) cyclopropane carboxylic acid, 8 cm$^3$ of tetrahydrofuran, 8 cm$^3$ of methylene chloride, 0.98 g of the alcohol obtained in Stage D and 30 mg of dimethylaminopyridine is cooled down to 0° C. 1.34 g of dicyclohexylcarbodiimide and 7 cm$^3$ of methylene chloride are added at 0° C. The resultant mixture is allowed to return to ambient temperature and is agitated for 4 hours. After filtration, the residue is rinsed and brought to dryness. 2.87 g of product is obtained which is chromatographed on silica, eluting with a hexane-ethyl acetate mixture (75-25). In this way 1.56 g of desired product is obtained.

Stage F: 1-[5-(difluoromethyl)-3-isoxazolyl] 2-propynyl 1R[1alpha,3alpha(Z)] 2,2-dimethyl 3-(3,3,3-trifluoro-2-chloropropenyl) cyclopropane carboxylate.

0.6 cm$^3$ of diethylaminosulphide trifluoride (DAST) is introduced at 0° C. into a solution containing 1.56 g of 1-[5-formyl-3-isoxazolyl] 2-propynyl 1R[1alpha,3alpha(Z)] 2,2-dimethyl-3-(3,3,3-trifluoro-2-chloropropenyl) cyclopropane carboxylate (obtained in Stage E). The reaction mixture is maintained under agitation for 4 hours at 20° C., and it is poured into a solution of sodium acid carbonate. Extraction is carried out with methylene chloride, the extracts are dried, filtered, rinsed and brought to dryness under reduced pressure. 1.81 g of a product is obtained which is chromatographed on silica, eluting with a hexane-ethyl acetate mixture (85-15). 1.39 g of desired product is obtained.

| NMR | |
| --- | --- |
| H of the twinned methyls | 1.28 |
| H$_1$ and H$_3$ | 1.08(d, J=8.5Hz) and 1.25(m) |
| H of C≡CH | 2.71(m) |
| H of CHF$_2$ | 6.76(t)(J=52.5Hz) |
| H of CO$_2$CHC=CH | 6.57(dd) |
| H of delta Z | 6.85(m) |

By operating as in Example 6, the following product was prepared:

EXAMPLE 7

1-(5-difluoromethyl-3-isoxazolyl)-2-propynyl [1R-[1alpha,3alpha(Z)]]-3-(3-ethoxy-2-fluoro-3-oxo-1-propenyl)-2,2-dimethylcyclopropane carboxylate.

| NMR CDCl$_3$ | |
| --- | --- |
| twinned methyls | 1.25 and 1.35 |
| H in positions 1 and 3 of the cyclopropane | 1.97(d, J=8.5Hz) and 2.95(m) |
| H of the ethynyl | 2.70(d, d) |
| H of delta E | 6.36(d, d J=10 and 21Hz) |

By operating as indicated in the preceding examples, starting with the appropriate acids and alcohols, the products of the following examples were prepared:

EXAMPLE 8

[3-(difluoromethyl) isoxazol-5-yl) methyl [1R-1alpha,3alpha(Z)]]-2,2-dimethyl 3-(2-chloro-3,3,3-trifluoro 1-propenyl) cyclopropane carboxylate.

Rf=0.2 (hexane-CH$_2$Cl$_2$ 6-4).

EXAMPLE 9

[3-(difluoromethyl) isoxazol-5-yl) methyl [1R-[1alpha,-3alpha(E)]]-2,2-dimethyl 3-(2-fluoro-3-methoxy 3-oxo 1-propenyl) cyclopropane carboxylate.
Rf=0.2 (hexane-isopropyl ether 7-3).

EXAMPLE 10

1-ethynyl [3-(difluoromethyl) isoxazol-5-yl) methyl [1R-[1alpha,3alpha(E)]]-2,2-dimethyl-3-(2-fluoro-3-methoxy 3-oxo 1-propenyl) cyclopropane carboxylate.
Rf=0.17 (hexane-acetone-$CH_2Cl_2$ 8-10-10).

EXAMPLE 11

1-ethynyl [3-(difluoromethyl) isoxazol-5-yl) methyl [1R-[1alpha,3alpha(Z)]]-2,2-dimethyl 3-(2-chloro-3,3,3-trifluoro 1-propenyl) cyclopropane carboxylate.
Rf=0.2 (hexane-isopropyl ether 9-1).

EXAMPLE 12

[3-(fluoromethyl) isoxazol-5-yl) methyl [1R-[1alpha,3alpha(Z)]]-2,2-dimethyl 3-(2-chloro-3,3,3-trifluoro 1-propenyl) cyclopropane carboxylate.
R=0.3 (hexane-acetone-$CH_2Cl_2$ 8-10-10).

EXAMPLE 13

[3-(fluoromethyl) isoxazol-5-yl) methyl [1R-[1alpha,3alpha(E)]]-2,2-dimethyl 3-(2-fluoro-3-methoxy 3-oxo 1-propenyl) cyclopropane carboxylate.
Rf=0.2 (hexane-isopropyl ether 6-4).

EXAMPLE 14

1-ethynyl [3-(fluoromethyl) isoxazol-5-yl) methyl [1R-[1alpha,3alpha(E)]]-2,2-dimethyl 3-(2-fluoro-3-methoxy 3-oxo 1-propenyl) cyclopropane carboxylate.
Rf=0.25 (hexane-ethyl acetate 9-1).

EXAMPLE 15

1-ethynyl [5-(formyl) isoxazol-3-yl) methyl [1R-[1alpha,3alpha(Z)]]-2,2-dimethyl 3-(2-chloro-3,3,3-trifluoro 1-propenyl) cyclopropane carboxylate.
Rf=0.2 (hexane-ethyl acetate 75-25).

EXAMPLE 16

1-ethynyl [5-(difluoromethyl) isoxazol-3-yl) methyl [1R-[1alpha,3alpha]] 3-(2,2-dichloroethenyl) 2,2-dimethyl cyclopropane carboxylate.
Rf=0.25 (hexane-ethyl acetate 9-1).

EXAMPLE 17

[5-(difluoromethyl) isoxazol-3-yl) methyl [1R-[1alpha,-3alpha(Z)]]-2,2-dimethyl 3-(2-chloro-3,3,3-trifluoro 1-propenyl) cyclopropane carboxylate.
Rf=0.2 (hexane-ethyl acetate 9-1).

EXAMPLE 18

[5-(difluoromethyl) isoxazol-3-yl) methyl [1R-[1alpha,-3alpha(E)]]-2,2-dimethyl 3-(2-fluoro-3-methoxy 3-oxo 1-propenyl) cyclopropane carboxylate.
Rf=0.2 (hexane-ethyl acetate 8-2).

EXAMPLE 19

[5-(methoxymethyl) isoxazol-3-yl) methyl [1R-[1alpha,-3alpha(E)]]-2,2-dimethyl 3-(2-fluoro-3-methoxy 3-oxo 1-propenyl) cyclopropane carboxylate.
Rf=0.2 (hexane-isopropyl ether 7-3).

EXAMPLE 20

[5-(methoxymethyl) isoxazol-3-yl) methyl [1R-[1alpha,-3alpha(Z)]]-2,2-dimethyl 3-(2-chloro-3,3,3-trifluoro 1-propenyl) cyclopropane carboxylate.
Rf=0.2 (hexane-ethyl acetate 8-2).

EXAMPLE 21

1-ethynyl [5-(methoxymethyl) isoxazol-3-yl) methyl [1R-[1alpha,3alpha(Z)]]-2,2-dimethyl 3-(2-chloro3,3,3-trifluoro 1-propenyl) cyclopropane carboxylate.
Rf=0.3 (hexane-ethyl acetate 8-2).

EXAMPLE 22

1-ethynyl [5-(methoxymethyl) isoxazol-3-yl) methyl [1R-[1alpha,3alpha(E)]]-2,2-dimethyl 3-(2-fluoro-3-ethoxy 3-oxo 1-propenyl) cyclopropane carboxylate.
Rf=0.2 (hexane-isopropyl ether 5-5).

EXAMPLE 23

[5-(methylthiomethyl) isoxazol-3-yl) methyl [1R-[1alpha,3alpha(Z)]]-2,2-dimethyl 3-(2-chloro-3,3,3-trifluoro 1-propenyl) cyclopropane carboxylate.
Rf=0.3 (hexane-ethyl acetate 8-2).

EXAMPLE 24

1-ethynyl [5-(methylthiomethyl) isoxazol-3-yl) methyl [1R-[1alpha,3beta(Z)]]-2,2-dimethyl 3-(2-fluoro-3-methoxy 3-oxo 1-propenyl) cyclopropane carboxylate.
Rf=0.15 (hexane-ethyl acetate 8-2).

EXAMPLE 25

[5-(methylthiomethyl) isoxazol-3-yl) methyl [1R-[1alpha,3beta(Z)]]-2,2-dimethyl 3-(2-fluoro-3-methoxy 3-oxo 1-propenyl) cyclopropane carboxylate.
Rf=0.15 (hexane-ethyl acetate 8-2).

EXAMPLE 26

1-ethynyl [5-(methylthiomethyl) isoxazol-3-yl) methyl [1R-[1alpha,3alpha(Z)]]-2,2-dimethyl 3-(2-chloro-3,3,3-trifluoro 1-propenyl) cyclopropane carboxylate.
Rf=0.35 (hexane-ethyl acetate 8-2).

EXAMPLE 27

[5-(dichloroethenyl) isoxazol-3-yl) methyl [1R-[1alpha,3beta(Z)]]-2,2-dimethyl 3-(2-fluoro-3-methoxy 3-oxo 1-propenyl) cyclopropane carboxylate.
Rf=0.15 (hexane-ethyl acetate 9-1).

EXAMPLE 28

[5-(dichloroethenyl) isoxazol-3-yl) methyl [1R-[1alpha,3beta(Z)]]-2,2-dimethyl 3-(2-chloro-3,3,3-trifluoro 1-propenyl) cyclopropane carboxylate.
Rf=0.2 (hexane-isopropyl ether 9-1).

EXAMPLE 29

1-ethynyl [5-(dichloroethenyl) isoxazol-3-yl) methyl [1R-[1alpha,3beta(Z)]]-2,2-dimethyl 3-(2-fluoro-3-methoxy 3-oxo 1-propenyl) cyclopropane carboxylate.
Rf=0.15 (hexane-ethyl acetate 85-15).

EXAMPLE 30

1-ethynyl [5-(dichloroethenyl) isoxazol-3-yl) methyl [1R-[1alpha,3alpha(Z)]]-2,2-dimethyl 3-(2-chloro-3,3,3-trifluoro 1-propenyl) cyclopropane carboxylate.
Rf=0.2 (hexane-ethyl acetate 9-1).

EXAMPLE 31

[3-(1-fluoro-1-prop-2-yn) isoxazol-5-yl] methyl [1R-[1alpha,3alpha(Z)]]-2,2-dimethyl 3-(2-chloro-3,3,3-trifluoro 1-propenyl) cyclopropane carboxylate.

Rf=0.2 (hexane-$CH_2Cl_2$ 5-5).

EXAMPLE 32

[3-(1-fluoro-1-prop-2-yn) isoxazol-5-yl] methyl [1R-[1alpha, 3alpha(E)]]-2,2-dimethyl 3-(2-fluoro-3-ethoxy 3-oxo 1-propenyl) cyclopropane carboxylate.

Rf=0.2 (hexane-isopropyl ether 8-2).

EXAMPLE 33

1-ethynyl [3-(fluoromethyl) isoxazol-5-yl] methyl [1R-[1alpha, 3alpha(Z)]]-2,2-dimethyl 3-(2-chloro-3,3,3-trifluoro 1-propenyl) cyclopropane carboxylate.

Rf=0.2 (hexane-ethyl acetate 9-1).

EXAMPLE 34

1-([5-(trifluoromethyl) isoxazol-3-yl] 2-propynyl [1R-[1alpha,3alpha(Z)]]-2,2-dimethyl 3-(3,3,3-trifluoro 2-chloropropenyl) cyclopropane carboxylate.

EXAMPLE 35

1-[3-(trifluoromethyl) isoxazol-5-yl] 2-propynyl [1R-[1alpha,3alpha(Z)]] 3-(2-chloro 3,3,3-trifluoro 1-propenyl) 2,2-dimethyl cyclopropane carboxylate.

Rf=0.23 (hexane-isopropyl ether 9-1).

EXAMPLE 36

1-[5-(trifluoromethyl) isoxazol-3-yl] 2-propynyl [1R-[1alpha,3alpha(E)]] 3-(2-fluoro 3-methoxy 3-oxo 1-propenyl) 2,2-dimethyl cyclopropane carboxylate.

EXAMPLE 37

1-[5-(trifluoromethyl) isoxazol-4-yl] 2-propynyl [1R-[1alpha,3alpha(Z)]] 3-(2-chloro 3,3,3-trifluoro 1-propenyl) 2,2-dimethyl cyclopropane carboxylate.

EXAMPLE 38

[5-(1-fluoro 2-propynyl) isoxazol-3-yl] methyl [1R-[1alpha,3alpha(Z)]] 3-(2-chloro 3,3,3-trifluoro 1-propenyl) 2,2-dimethyl cyclopropane carboxylate.

Rf=0.2 (hexane-isopropyl ether 9-1).

EXAMPLE 39

[5-(1-fluoro-2-propynyl) isoxazol-3-yl] methyl [1R-[1alpha,3alpha(E)]] 3-(3-ethoxy 2-fluoro 3-oxo 1-propenyl) 2,2-dimethyl cyclopropane carboxylate.

Rf=0.12 (hexane-ethyl acetate 85-15).

EXAMPLE 40

Preparation of a soluble concentrate
A homogeneous mixture is made of:

| | |
|---|---|
| Product of Example 6 | 0.25 g |
| Piperonyl butoxide | 1.00 g |
| Tween 80 | 0.25 g |
| Topanol A | 0.1 g |
| Water | 98.4 g |

EXAMPLE 41

Preparation of an emulsifiable concentrate
The following are intimately mixed:

| | |
|---|---|
| Product of Example 2 | 0.015 g |
| Piperonyl butoxide | 0.5 g |
| Topanol A | 0.1 g |
| Tween 80 | 3.5 g |
| Xylene | 95.885 g |

EXAMPLE 42

Preparation of an emulsifiable concentrate
A homogeneous mixture is made of:

| | |
|---|---|
| Product of Example 6 | 1.5 g |
| Tween 80 | 20.00 g |
| Topanol A | 0.1 g |
| Xylene | 78.4 g |

EXAMPLE 43

Preparation of granules
Granules were prepared containing 0.1% to 5% of active substances.

BIOLOGICAL STUDY

A. Activity on Diabrotica

The test insects are final-stage Diabrotica larvae.

A 9 cm diameter disc of filter paper, placed at the bottom of a Petri dish, is treated with 2 $cm^3$ of an acetonic solution of the product to be tested. After drying, 10 larvae per dose are deposited and the mortality check is carried out 24 hours after the treatment.

From a dose of 0.5 ppm, the products of the invention show a good activity.

B. Study of the knock-down effect on the housefly

The test insects are 4-day old female houseflies. The operation is carried out by spraying in a Kearns and March chamber using a mixture of acetone (5%) and Isopar L (petroleum solvent) as solvent (quantity of solvent used 2 ml per second). 50 insects per treatment are used. Checks are carried out every minute up to 10 minutes, then at 15 minutes and the KT 50 is determined by the usual methods.

At a dose of 1 g/liter, the products of the invention show a good activity.

We claim:

1. A compound in all possible stereoisomer forms and mixtures thereof of the formula

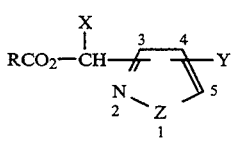

I wherein

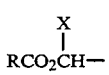

is in position 3 or 5, X is selected from the group consisting of hydrogen, —CN and alkyl, alkenyl and alkynyl of up to 4 carbon atoms, Y is in position 4 or 5 and is selected from the group consisting of hydrogen, —CN, —$NO_2$, —$NH_2$, alkyl, alkenyl and alkynyl of up to 8 carbon atoms optionally substituted with at least one halogen, —(CH$_2$)$_n$—OH, —CH$_2$OCH$_3$, —CH$_2$OCOCH$_3$,

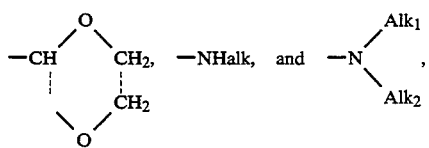—NHalk, and n is 0, 1,2,3, or 4, Alk$_1$ and Alk$_2$ are individually alkyl of 1 to 8 carbon atoms, Z is —O— or —S—, with the proviso that when X is ethynyl, R is selected from the group consisting of

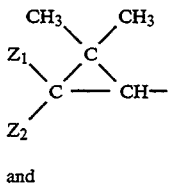

and

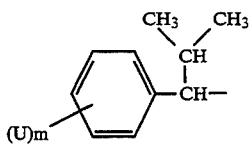

and Z$_1$ and Z$_2$ are both methyl or Z$_1$ is hydrogen and Z$_2$ is selected from the group consisting of

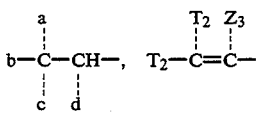

and

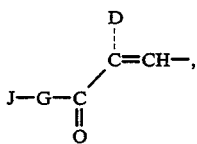

Z$_3$ is hydrogen or halogen, T$_1$ and T$_2$ are individually selected from the group consisting of hydrogen, halogen, alkyl and alkoxy of 1 to 8 carbon atoms optionally substituted with at least one halogen, —CH$_2$F, —CHF$_2$, —CF$_3$, —CN and phenyl optionally substituted by halogen or T$_1$ and T$_2$ form cycloalkyl of 3 to 6 carbon atoms or

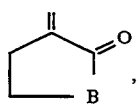

is —O— or —S—, a,b,c and d are individually halogen, D is selected from the group consisting of hydrogen and alkoxy of 1 to 8 carbon atoms, G is —O— or —S—, J is selected from the group consisting of alkyl, alkenyl and alkynyl of up to 8 carbon atoms, cycloalkyl of 3 to 8 carbon atoms, all optionally substituted with at least one fluorine, aryl of 6 to 14 carbon atoms optionally substituted with at least one functional group, pyridyl, furyl, thienyl and oxazolyl, U is selected from the group consisting of halogen, alkyl and alkoxy of 1 to 8 carbon atoms, m is 0, 1 or 2 and when m is 2, the Us may be different and when X is hydrogen or cyano or alkyl, alkoxy or alkynyl other than ethynyl of up to 8 carbon atoms, R is selected from the group consisting of

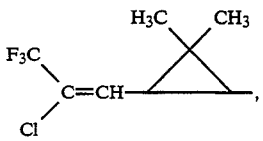

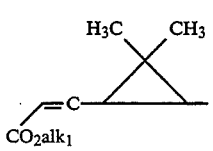

and

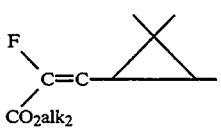

2. The compounds of formula (I) as defined in claim 1 in which Z represents an oxygen atom.

3. The compounds of formula (I) as defined in claim 2 in which the

is in position 3.

4. The compounds of formula (I) as defined in claim 1 in which X represents an ethynyl radical.

5. The compounds of formula (I) as defined in any one of claims 1 to 3 in which X represents a hydrogen atom.

6. The compounds of formula (I) as defined in claim 1 in which Y is in position 5.

7. The compounds of formula (I) as defined in claim 1 in which Y represents a saturated or unsaturated alkyl radical containing up to 4 carbon atoms optionally substituted by one or more halogen atoms.

8. The compounds of formula (I) as defined in claim 7 in which Y represents a CHF$_2$ radical.

9. The compounds of formula (I) as defined in claim 7 in which Y represents a CF$_3$, CH$_3$, CH$_2$F or

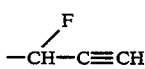

radical.

10. The compounds of formula (I) as defined in claim 1 in which R represents the radical:

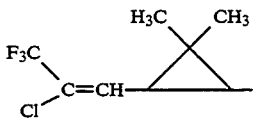

in all their possible stereoisomer possible as well as their mixtures.

11. The compounds of formula (I) as defined in claim 1 in which R represents a radical:

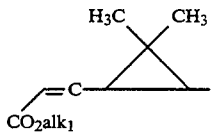

in which-alk$_1$ represents an alkyl radical containing up to 4 carbon atoms optionally substituted by one or more fluorine atoms.

12. The compounds of formula (I) as defined in claim 1 in which R represents

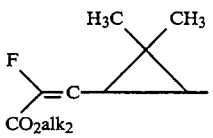

in which alk$_2$ represents an alkyl radical containing up to 4 carbon atoms optionally substituted by one or more fluorine atoms.

13. The compounds of formula (I) as defined in claim 1 of which the names follow:
- -5-(difluoromethyl alpha-ethynyl 3-isoxazolyl) methyl 1R[1alpha,3alpha(Z)] 2,2-dimethyl 3-(3,3,3-trifluoro 2-chloro propenyl) cyclopropane carboxylate,
- -(5-methyl-3-isoxazolyl) methyl [1R-[1alpha,3alpha(Z)]]-3-(3-ethoxy-2-fluoro-3-oxo-1-propenyl)-2,2-dimethylcyclopropane carboxylate,
- -1-(5-difluoromethyl-3-isoxazolyl)-2-propynyl [1R-[1alpha,3alpha(Z)]]-3-(3-ethoxy-2-fluoro-3-oxo-l-propenyl)-2,2-dimethylcyclopropane carboxylate,
- -[3-(1-fluoro-1-prop-2-yn) isoxazol-5-yl] methyl [1R-[1alpha,3alpha(E)]]-2,2-dimethyl 3-(2-fluoro-3-ethoxy 3-oxo 1-propenyl) cyclopropane carboxylate,
- 1-ethynyl [3-(fluoromethyl) isoxazol-5-yl] methyl [1R-[1alpha,3alpha(E)]]-2,2-dimethyl 3-(2-chloro-3,3,3-trifluoro 1-propenyl) cyclopropane carboxylate,
- -1-[5-(trifluoromethyl) isoxazol-3-yl)-2-propynyl [1R-[1alpha,3alpha(Z)]]-2,2-dimethyl 3-(3,3,3-trifluoro 2-chloropropenyl) cyclopropane carboxylate, in all their possible stereoisomer forms as well as their mixtures.

14. Compositions intended for combating parasites of vegetation, parasites in premises and parasites of warm-blooded animals, characterized in that they contain as active ingredient at least one compound defined in claim 1.

15. Insecticide compositions, characterized in that they contain as active ingredient at least one compound defined in claim 1.

16. Insecticide compositions defined in claim 15, characterized in that they are intended for combating DIABROTICA and other parasites of the soil.

17. Acaricide compositions, characterized in that they contain as active ingredient at least one compound defined in claim 1.

18. Combinations endowed with insecticide, acaricide or nematicide activity, characterized in that they contain as active ingredient, on the one hand at least one of the compounds of general formula (I), claim 1 and on the other hand at least one of the pyrethrinoid esters chosen from the group constituted by the esters of allethrolone, of 3,4,5,6-tetrahydrophthalimidomethyl alcohol, of 5-benzyl-3-furyl methyl alcohol, of 3-phenoxybenzyl alcohol and of alphacyano-3-phenoxybenzyl alcohol with chrysanthemic acids, by the esters of 5-benzyl-3-furyl methyl alcohol with 2,2-dimethyl-3-(2-oxo-3-tetrahydrothiophenylidenemethyl)-cyclopropanecarboxylic acids, by the esters of 3-phenoxybenzyl alcohol and of alpha-cyano-3-phenoxybenzyl alcohol with 2,2-dimethyl-3-(2,2-dichlorovinyl)-cyclopropanecarboxylic acids, by the esters of alpha-cyano-3-phenoxy-benzyl alcohol with 2,2-dimethyl-3-(2,2-dibromovinyl)-cyclopropanecarboxylic acids, by the esters of 3-phenoxybenzyl alcohol with 2-para-chlorophenyl-2-isopropyl acetic acids, by the esters of allethrolone, of 3,4,5,6-tetrahydrophthalimidomethyl alcohol, of 5-benzyl-3-furyl methyl alcohol, of 3-phenoxybenzyl alcohol, and of alphacyano-3-phenoxybenzyl alcohol with 2,2-dimethyl-3-(1,2,2,2-tetrahaloethyl)-cyclopropanecarboxylic acids, in which "halo" represents a fluorine, chlorine or bromine atom, it being understood that the compounds (I) can exist in all their possible stereoisomer forms as well as the acid and alcohol copulas of the above pyrethrinoid esters.

19. A method of combatting insects comprising contacting insects with an insecticidally effective amount of at least one compound of claim 1.

* * * * *